United States Patent
Kaito (10) Patent No.: US 8,728,286 B2
(45) Date of Patent: May 20, 2014

(54) METHOD OF MANUFACTURING SAMPLE FOR ATOM PROBE ANALYSIS BY FIB AND FOCUSED ION BEAM APPARATUS IMPLEMENTING THE SAME

(75) Inventor: Takashi Kaito, Chiba (JP)

(73) Assignee: SII Nano Technology Inc., Chiba (JP)

( * ) Notice: Subject to any disclaimer, the term of this patent is extended or adjusted under 35 U.S.C. 154(b) by 1740 days.

(21) Appl. No.: 11/936,417

(22) Filed: Nov. 7, 2007

(65) Prior Publication Data

US 2008/0289954 A1    Nov. 27, 2008

(30) Foreign Application Priority Data

Nov. 9, 2006    (JP) .................... 2006-303500

(51) Int. Cl.
| | | |
|---|---|---|
| C23C 14/00 | (2006.01) | |
| C23C 14/32 | (2006.01) | |
| B44C 1/22 | (2006.01) | |
| C03C 15/00 | (2006.01) | |
| C03C 25/68 | (2006.01) | |
| C23F 1/00 | (2006.01) | |
| C23F 3/00 | (2006.01) | |
| C23C 14/04 | (2006.01) | |
| C23C 14/14 | (2006.01) | |
| G01Q 60/38 | (2010.01) | |
| G01Q 70/10 | (2010.01) | |
| G01Q 70/12 | (2010.01) | |
| B82Y 35/00 | (2011.01) | |
| G01N 1/32 | (2006.01) | |

(52) U.S. Cl.
CPC .............. *G01Q 60/38* (2013.01); *G01Q 70/10* (2013.01); *G01Q 70/12* (2013.01); *B82Y 35/00* (2013.01); *G01N 1/32* (2013.01); *H01J 2237/20* (2013.01); *H01J 2237/3109* (2013.01); *H01J 2237/31732* (2013.01); *H01J 2237/3174* (2013.01)
USPC .......... 204/192.34; 216/66; 216/94; 427/523; 427/526; 427/531

(58) Field of Classification Search
CPC ....... B82Y 35/00; G01N 1/32; H01J 2237/20; H01J 2237/3109; H01J 2237/31732; H01J 2237/3174; G01Q 60/38; G01Q 70/10; G01Q 70/12
USPC .......... 204/192.34; 216/66, 94; 427/523, 526, 431
See application file for complete search history.

(56) References Cited

U.S. PATENT DOCUMENTS 6,953,519 B2 * 10/2005 Shirakawabe et al. ... 204/192.32

FOREIGN PATENT DOCUMENTS

JP    2005-265516 A    9/2005

* cited by examiner

*Primary Examiner* — Michael Band
(74) *Attorney, Agent, or Firm* — Brinks Gilson & Lione (57) ABSTRACT

A method of manufacturing a sample for an atom probe analysis of the invention is made one going through a step of manufacturing a concave/convex structure in both of a base needle and a transplantation sample piece by an etching working of an FIB, a step of jointing mutual members, and a step of bonding such that the concave/convex structure becomes a mesh form by a deposition working of the FIB.

7 Claims, 6 Drawing Sheets

METHOD OF MANUFACTURING SAMPLE FOR ATOM PROBE ANALYSIS BY FIB AND FOCUSED ION BEAM APPARATUS IMPLEMENTING THE SAME

RELATED APPLICATIONS

This application claims priority under 35 U.S.C. §119 to Japanese Patent Application No. JP2006-303500 filed on Nov. 9, 2006, the entire content of which is hereby incorporated by reference.

BACKGROUND OF THE INVENTION

The present invention relates to a method of manufacturing a sample for an atom probe analysis by an FIB, and an apparatus capable of easily implementing that method.

Figure 7:
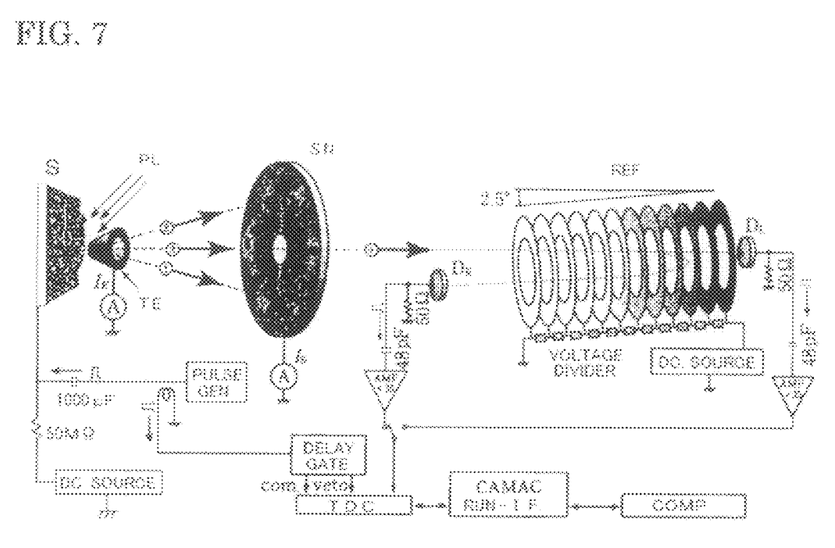
FIG. 7 is a view explaining a basic constitution of a scanning atom probe.

As means capable of directly observing an atomic arrangement of a needle point, there is developed an atom probe (AP: Atom Probe) that is a composite instrument of a mass spectrometer capable of detecting a single ion and a field-ion microscope (FIM). The AP is a solitary device capable of analyzing an electronic state, the atomic arrangement and a composition distribution of the needle point. Since a field evaporation orderly proceeds in every atom layer from a surface first layer, by the AP it is possible to investigate a composition or the composition distribution of an interface, and additionally an electronic state change in every layer. However, for this AP, there is a strict restriction in a manufacture and a shape of a sample, so that a field in which its characteristic can be practically used is limited. One devised in order to break down this restriction is a scanning atom probe (SAP: Scanning Atom Probe). In order to select a specified needle from needles densely arranged and investigate its tip, an electric field must be localized to the needle point. Whereupon, a grounded fine funnel type leader electrode is attached to an inside of a housing of the AP, and a positive voltage is applied to a planar sample in which fine needles are densely arranged. Thereupon, a high electric potential generates in a single needle point existing just below a hole, whose diameter is several μm to several tens μm, in a tip of the leader electrode, and the electric field is localized to a very narrow space between the hole and the needle point. According to an electric field distribution calculation by a computer, even if an apex angle of the needle point is 90° and a tip curvature radius is 50 nm, in the needle point there is generated the high electric field demanded in an electric field radiation and the field evaporation. This fact shows the fact that, if a concave/convex of about several μm exists on a flat sample face, it is possible to analyze a tip of its protrusion. Since a surface to which there is applied no flattening processing, a corroded surface, a surface of highly efficient catalyst, and the like are normally rich in the concave/convex, it follows that these surfaces are investigates as they are. In FIG. 7, there is shown a basic structure of the SAP. A sample S in a left end is one showing schematically a densely arranged type electric field radiation electron source. If a hole in a tip of a funnel type leader electrode TE approaches to a tip of the needle point or the protrusion on the sample face, the high electric potential generates in a very narrow region between the tip and the electrode, and electrons radiated from the needle point project an FEM image to a screen SN. Further, if an inert image gas such as helium is introduced into the housing and the positive voltage is applied to the sample S, an FIM image of a high resolving power is projected to the screen SN. Additionally, if a surface atom is field-evaporated by superimposing a pulse voltage onto a steady-state voltage or irradiating a pulse laser light PL to the sample face, the surface atom evaporated as a positive ion enters into a reflectron REF that is the mass spectrometer while passing through an exploration hole in a center of the screen SN, and is detected one by one. A region to be analyzed is a region, whose diameter is several nanos to several tens nanos, of a protrusion tip corresponding to the exploration hole. If the analysis is continued, it is possible to investigate a composition change in a depth direction of this region with a resolving power of one atom layer.

If the sample having in its surface the concave/convex, especially a convex portion, is found, it is opposed to the leader electrode, the sample protrusion part is field-evaporated in order from an upper layer atom, and it is drawn out as the ion and detected by an ion detector (two-dimensional detection type) disposed rearward the leader electrode, since an element analysis is possible by a time-of-flight measurement of each ion and also a position information is obtained, a three-dimensional composition analysis in an atomic level is possible. In a case where an analysis object sample of a semiconductor wafer, a thin film magnetic head wafer called GMR or TMR, for which there are strong needs, or the like is made the sample, it is frequent that it becomes a multi-layered structure in which complicated patterns are overlapped, and a structure of a portion desired to be analyzed is various. In order to analyze the analysis object like this by using the AP, although it is necessary to locally cut out a place desired to be analyzed and fix it to a tip of a needle-like protrusion becoming an electrode while being cut out as a fine section, hitherto there merely exists only a conventional method of making a sample of metal material or the like into needle-like one, so that it is very difficult to analyze a fine specified site by the AP. Therefore, as a technique replaceable with this, a development in a preliminary working technique working the sample itself like the needle becomes indispensable. With a relation that it is the analysis in the atomic level, since an analysis object dimension becomes about 100 cubic nm, a technique for manufacturing a analysis object part to a needle-like sample in a pinpoint becomes very important.

As one responding to such needs, the present inventor previously presented JP-A-2005-265516 Gazette entitled "Atom probe apparatus and its sample preliminarily working method", published on Sep. 29, 2005. Problems of this invention are to present a technique of a sample preliminarily working in which a place desired to be analyzed of a device is locally cut out to thereby be made a needle-like protrusion, and to present a technique in which, even if it is a sample of a multi-layered structure including an atom layer of a small evaporation electric field in a certain circumstance, an orderly stable ion evaporation is made possible, thereby making an SAP analysis in the atomic level possible. And, the preliminary working of the sample for the atom probe apparatus of this invention comprises a step of cutting out, like a block, a sample desired observation site by using a focused ion beam (FIB) apparatus, a step of temporarily bonding the cut-out block-like sample by an FIB-CVD, a step of making a notch over a base part of the block-like sample and a sample substrate by an FIB etching, a step of bonding/fixing the sample substrate and the block-like sample by applying thereafter the FIB-CVD to the notched portion, and a step of working the block-like sample fixed on the sample substrate into a needle point shape by an FIB etching working. Further, the sample worked into the needle point shape is one worked such that a layer direction in the multi-layered structure becomes parallel to a longitudinal direction of a needle.

As to an AP sample needle, since it is necessary to concentrate an electric field to the tip, although it is necessary to transplant a sample piece onto a base metal needle or a base Si circular cone pillar, one making it possible is a sample piece picking/transplanting technique by the above FIB. This technique is one in which a transmission electron microscope (TEM) sample thin piece manufacturing technique is applied. However, in this sample piece picking/transplanting technique, there is the fact that there generates such an issue that, by a strong electrostatic attraction force at an AP analysis time, a transplantation piece in a front from a joint part flies and is lost. This issue is one generating because a strength of an interface between a deposition film and a material to be bonded, which are bonded by the FIB-CVD, is insufficient and they are exfoliated.

A problem of the invention is to solve the above issue, i.e., to present, in a transplanting/bonding method of an atom probe sample piece, a firm bonding/fixing technique of the sample substrate and the block-like sample, which can sufficiently withstand the strong electrostatic attraction force at the AP analysis time.

SUMMARY OF THE INVENTION

A method of manufacturing a sample for an atom probe analysis of the invention comprises a step of manufacturing a concave part or a convex part in side walls of both of a base needle and a transplantation sample piece by an etching working of an FIB, and a step of bonding the base needle and the transplantation sample piece by making them a mesh state by utilizing the concave part or the convex part, or providing an FIB deposition film so as to become the mesh state.

One mode of a method of manufacturing a sample for an atom probe analysis of the invention is one in which a concave/convex structure is manufactured in side walls of both of the base needle and the transplantation sample piece by the etching working of the FIB, and there is made so as to bond, under a state jointed such that a concave and a convex are mutually meshed, by providing around it a CVD deposition film using the FIB. And, as an example of the concave/convex structure, there is made such that it is a penetration groove of side walls of both of the base needle and the transplantation sample piece, or a convex part extending between the side walls.

Further, other mode of a method of manufacturing a sample for an atom probe analysis of the invention is one in which, under a state in which end faces of the base needle and the transplantation sample piece are joint-butted, grooves are worked in both-member positions slightly separated from the jointed faces of both of the base needle and the transplantation sample piece by the etching working of the FIB, and is made one in which the deposition film is formed and bonded by a deposition working of the FIB so as to extend over these grooves.

The concave part is a circumference-like groove or a quadrate hole.

A focused ion beam apparatus of the invention, which implements a method of manufacturing a sample for an atom probe analysis, is one in which a jig, in which a metal tube retaining a base needle by being caulked is attached to a rectangular material groove-worked such that this tube is fitted, is installed on a stage having an electric motored five-axis, and the jig is made one possessing a function capable of switching a slant at least between 0° and 90°.

Further, in its one mode, there is made one in which a member retaining the base needle possesses a function capable of rotating about a needle axis, in addition to the function capable of switching the slant.

Since the method of manufacturing the sample for the atom probe analysis of the invention is one in which the concave/convex structure is manufactured in both of the base needle and the transplantation sample piece by the etching working of the FIB, and there is bonded by the deposition working of the FIB such that the concave/convex structure becomes a mesh form by jointing mutual members, a joint strength is greatly raised, so that it is possible to sufficiently withstand the strong electrostatic attraction force at the AP analysis time.

Since the focused ion beam apparatus of the invention, which implements the method of manufacturing the sample for the atom probe analysis, is made one in which the member retaining the base needle additionally possesses, on the stage having the electric motored five-axis, the function capable of rotating about the needle axis and the function capable of switching the slant at least between 0° and 90°, by using freely the rotation function and the slant function it is possible to easily implement a transplanting/bonding method of the atom probe sample piece of the invention. Further, since there is adopted a form in which the member retaining the base needle is installed on the stage having the electric motored five-axis, there can be easily provided only by performing a working for attaching the retention member to an existing FIB apparatus.

DETAILED DESCRIPTION OF THE PREFERRED EMBODIMENTS

Figure 6A:
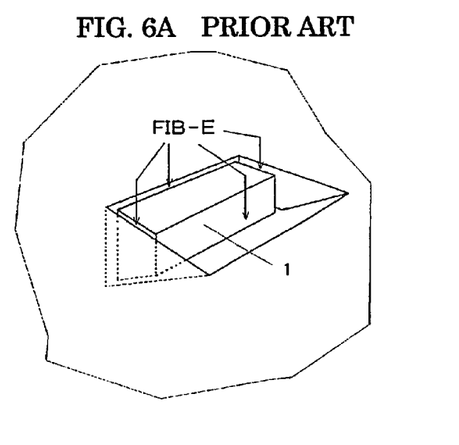
FIGS. 6A-6E are views explaining conventional processes from a cutting-out to a fixation to a base and a sharpening working of a sample.
Figure 6B:
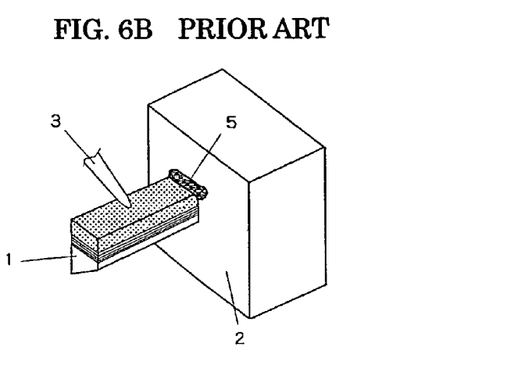
Figure 6C:
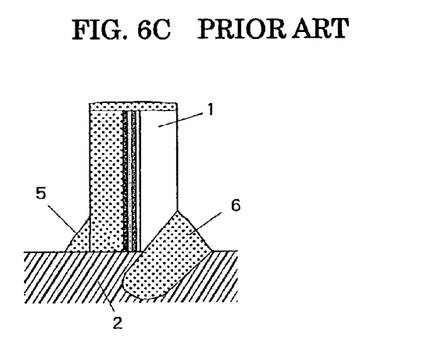
Figure 6D:
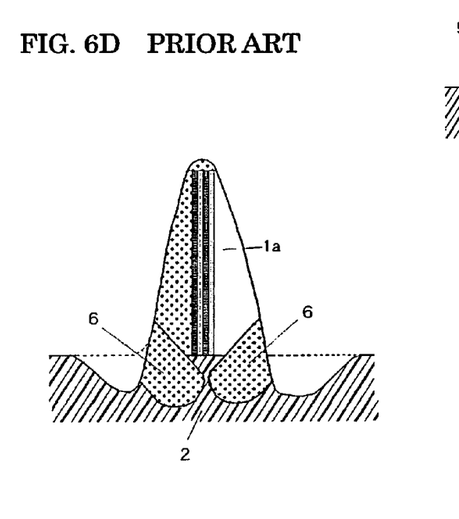
Figure 6E:
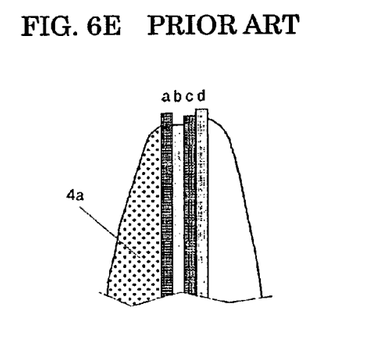

Before explaining an embodiment of the invention, a working method introduced in the Patent Document 1 is previously explained while referring to FIGS. 6A-6E. As shown in FIG. 6A, a four-direction periphery of an observation desired place is boring-worked by an FIB etching, and a bottom cut by the FIB etching is performed by tilting a sample stage such that an FIB irradiation can be performed from a direction along which a large hole is bored, thereby cutting off from a device. A cut-off block-like analysis sample piece 1 is carried onto a fixation base 2 by a fine probe 3 operated by a manipulator as shown in FIG. 6B, and temporarily fixed by an FIB-CVD. If a place desired to be observed is specified and the cut-out block-like sample piece 1 is temporarily fixed (temporal fixation part 5) onto a fixation substrate by the FIB etching, a notch is made over a base part of the block-like sample piece 1 and the fixation base 2 by the FIB etching by tilting the sample stage. Thereafter, by applying the FIB-CVD to that notch portion, a sample substrate and the block-like sample are really bonding-fixed (real fixation part 6). This state is shown in FIG. 6D. By applying this real fixation to plural places, the block sample piece 1 is firmly fixed to the fixation base 2. Finally, this block-like sample piece 1 is formation-worked to a needle shape by the FIB etching. A needle-like sample 1a preliminarily worked by doing like this is shown in FIG. 6E. Here, as shown in FIG. 6B, although the fixation base 2 is made a flat plate larger than the cut-out sample piece 1, there may be worked such that a whole becomes like a large needle by previously providing a needle-like protrusion (base needle), whose tip is made flat, in the fixation base 2 and fixing thereon the cut-out sample piece 1.

Like the above, the working method introduced in the Patent Document 1 is one in which a hole penetrating through both the sample substrate and the sample is bored and a filling-working is performed to that portion by a deposition. However, as mentioned before, in this bonding/fixing technique, it is impossible to withstand the strong electrostatic attraction force at the AP analysis time, so that there is the fact that such an accident rarely occurs that the joint part is exfoliated and the transplantation piece flies. Whereupon, the invention presents a firm bonding/fixing technique of a sample base part and the block-like sample, which is additionally solid.

Embodiment 1

Figure 1A:
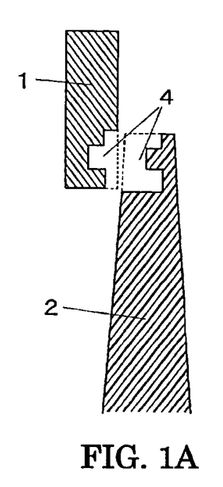
FIGS. 1A-1C are views schematically showing a first bonding/fixing technique concerned with the invention.
Figure 1B:
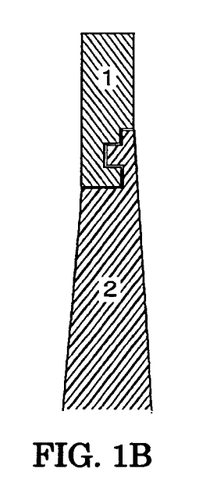
Figure 1C:
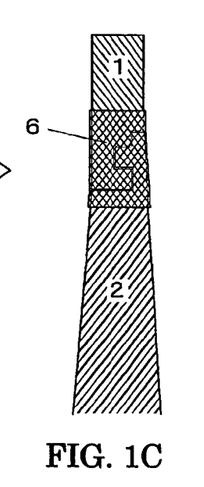

First, a first bonding/fixing technique concerned with the invention is explained while referring to FIGS. 1A-1C. In the drawing, 1 is a cut-off block-like observation sample piece, and it is carried to a tip portion of a base needle 2 by a fine probe operated by the manipulator similarly to the conventional technique shown in FIG. 6B. Although FIG. 1A is a form at this time, in tip portions of a base part of the observation sample piece 1 and the base needle 2, a mutually meshing concave/convex shape 4 is already engraved. The concave shape 4 is formed by the etching working by the FIB under a state in which the observation sample piece 1 is fixed to a tip of the fine probe by the FIB-CVD. The convex shape 4 is formed by the etching working by the FIB under a state in which a tip portion of the base needle 2 is retained by a base needle retention member attached to an FIB apparatus mentioned later. As shown in FIG. 1B, these both members are fitted with the concave and convex being meshed. This work is operated by the manipulator, and realized by being moved such that the observation sample piece 1 meshes with the tip portion of the base needle 2. If a fit is performed, a deposition working is performed by the FIB-CVD so as to coat a periphery of that meshed portion by a deposition layer 6. A form fixed by this deposition layer 6 is shown in FIG. 1C. Since the mutual concave/convex shape meshes, an endurance force is reinforced in regard to a force applied to the tip portion of the sample piece and a tensile force in a needle axis direction, so that a solid bonding/fixing is realized.

In schematic views of FIG. 1A-1C, there is shown one in which there is formed a groove penetrating through both side faces in a direction perpendicular to a needle axis or a convex part formed over the both side faces. When the concave shape adopts a groove structure, if a direction of the groove is the same direction as the needle axis, as to the observation sample piece 1 fixed with the concave and the convex being meshed, since the endurance force is not reinforced in regard to the tensile force in the needle axis direction, the groove is worked in a perpendicular direction in order to realize the solid bonding/fixing.

In FIGS. 1A-1C, a groove part is provided also in both sides of the concave or convex part 4 of the observation sample piece 1 and the base needle 2, thereby increasing a meshing part. By this, there can be strongly bonding-fixed.

Embodiment 2

Figure 2A:
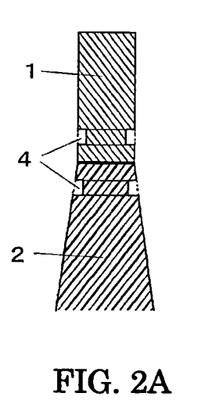
FIGS. 2A-2C are views schematically showing a second bonding/fixing technique concerned with the invention.
Figure 2B:
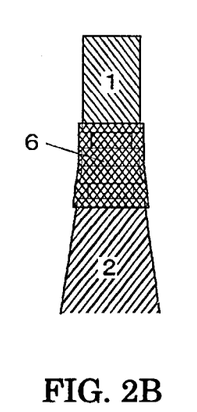
Figure 2C:
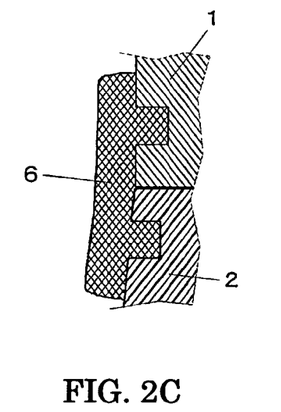

A second bonding/fixing technique concerned with the invention is explained while referring to FIGS. 2A-2C. A form shown in FIG. 2A is a state in which a flat base part of the observation sample piece 1 is butt-jointed to a flat tip portion of the base needle 2 and, in both members, there is formed a circumference-like groove 4 as the concave/convex shape in a position slightly spaced from the joint face. As to this groove working, similarly to the previous example, the groove shape 4 may be formed by the etching working by the FIB under the state in which the observation sample piece 1 is fixed to the tip of the fine probe by the FIB-CVD, or the groove shape 4 may be formed by the etching working by the FIB under the state in which the tip portion of the base needle 2 is retained by the base needle retention member attached to the FIB apparatus, or there may be made so as to form the groove by temporarily fixing, under a state butt-jointed in raw intact, its joint portion by the deposition working by the FIB-CVD, and implementing the groove working of both members by the etching working by the FIB under a state retained by the base needle retention member. Next, as shown in FIG. 2B, the deposition layer 6 is formed so as to extend over the grooves 4 of both members by a deposition working of the FIB, and fixed. A sectional shape of this deposition layer 6 formed so as to extend over the grooves 4 of both members is shown in FIG. 2C while being enlarged. Like this, since both members are connected while extending over both the groove parts 4 in a U-shaped clamp form, the endurance force is reinforced in regard to the force applied to the tip portion of the sample piece and the tensile force in the needle axis direction, so that the solid bonding/fixing is realized.

Embodiment 3

Figure 3A:
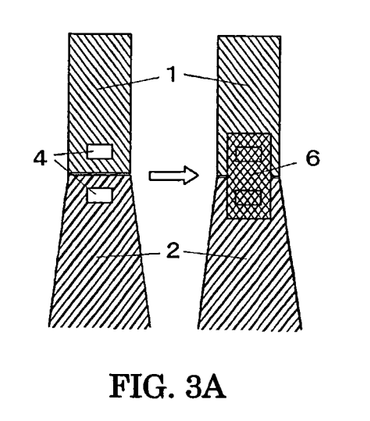
FIGS. 3A and 3B are views schematically showing two modified examples of the second bonding/fixing technique concerned with the invention.
Figure 3B:
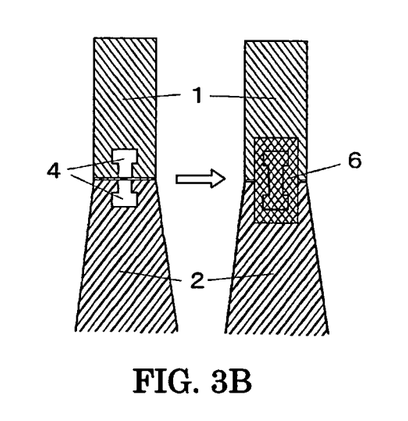

Two modified examples of the second bonding/fixing technique concerned with the invention are explained while referring to FIGS. 3A and 3B. In the previous example, although it is one which is under the state in which the flat base part of the observation sample piece 1 is butt-jointed to the flat tip portion of the base needle 2 and in which there is formed the circumference-like groove 4 in both-member positions slightly spaced from the joint face by the etching working of the FIB, the modified example shown here is one in which a hole is bored, not the groove. An embodiment shown in FIGS. 3A and 3B is one in which a quadrate hole 4 having faces intersecting perpendicularly to the needle axis is provided in both members by the etching working of the FIB. The deposition layer 6 is formed by the deposition working of the FIB so as to extend over these quadrate holes 4 formed in both members, and they are fixed by a bridge of the clamp form. A left side of FIG. 3A is a view showing a form in which both members provided with the holes 4 are butt-jointed, and a right side is a view showing a form in which they are connected by the deposition layer 6 so as to extend over both the holes 4. The bridge of the clamp form like this is worked in plural places in a circumferential direction of the needle.

An embodiment shown in FIG. 3B is one in which the quadrate hole 4 having faces intersecting perpendicularly to the needle axis is provided in both members while being made the concave shape by the etching working of the FIB, and an I-shaped continuous hole is provided by connecting both the holes 4 by a groove. The deposition layer 6 is formed by the deposition working of the FIB so as to coat this I-shaped continuous hole portion, and they are connection-fixed by an I-shaped bridge. A left side of FIG. 3B is a view showing a form in which the I-shaped continuous hole is provided by connecting both the holes 4 by the groove and both members are butt-jointed, and a right side is a view showing a form in which they are connected by the deposition layer 6 of the I-shaped bridge so as to extend over both the holes 4. Also in this embodiment, the bridge of the clamp form is worked in plural places in the circumferential direction of the needle.

Since these two embodiments are ones in which the joint faces of both members are connected by forming such a bridge as to extend over the quadrate holes 4 having the faces intersecting perpendicular to the needle axis direction in the plural places in the circumferential direction, the endurance force is reinforced in regard to the force applied to the tip portion of the sample piece and the tensile force in the needle axis direction, so that the solid bonding/fixing is realized.

Figure 4A:
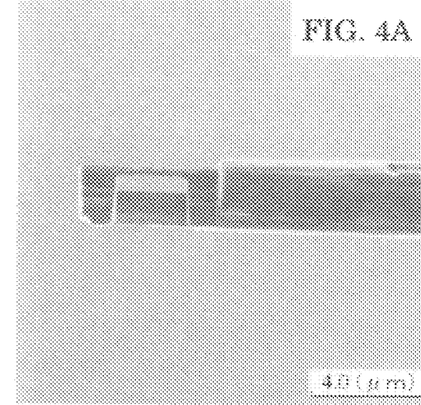
FIGS. 4A-4F are FIB photomicrographs in which there are photographed processes by which a sample, which is fixed to a base needle and whose tip part is sharpened, is gradually manufactured by the first bonding/fixing technique concerned with the invention.
Figure 4B:
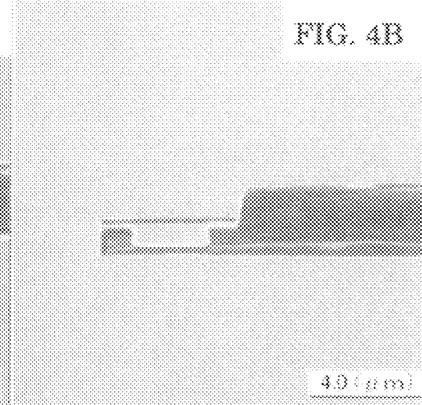

In FIGS. 4A-4F, there is shown an FIB photomicrograph of a sample actually FIB-worked by the first bonding/fixing technique concerned with the invention. If procedures of a sample manufacture of the invention are explained, a first step is a work cutting out the observation sample similarly to the conventional technique shown in FIG. 6A. Subsequently, a second step is a work fixing the base part of the sample piece 1 to the tip part of the probe 3 operated by the manipulator, by the deposition. A third step is a work etching-working the concave/convex shape to the base part of the sample piece 1 fixed to the probe 3. Although an image of this worked sample is not shown, it is approximately similar to a working, of the base needle 2, shown next. Subsequently, a fourth step is a work etching-working the concave/convex shape to the tip part of the base needle 2. Ones shown in FIG. 4A and FIG. 4B are ones in which the working of the concave/convex shape is applied to the tip part of the base needle 2, and FIG. 4A and FIG. 4B are images taken by rotating a direction of the sample by 90° in the axial direction. A length of a lower-right index is a scale that is 4.0 µm. In schematic views of FIGS. 1A-1B, although there is shown one in which the simple groove penetrating to both side faces is formed in each member, in the sample of this photograph, a butting part is left in a side face part of one member, and a side face of the other member is worked in a shape positioned while butting against there. Since an image in which the FIB is being scanned is a plane image, although a two-dimensional positional alignment is possible, a position cannot be grasped in a depth direction. A reason why such a workmanship is applied is for facilitating the positional alignment in the depth direction. Incidentally, in a case where a composite machine possessing an SEM lens tube is possessed besides an FIB lens tube, since it is possible to grasp a depth information as well, the workmanship like this is not necessarily required.

Figure 4C:
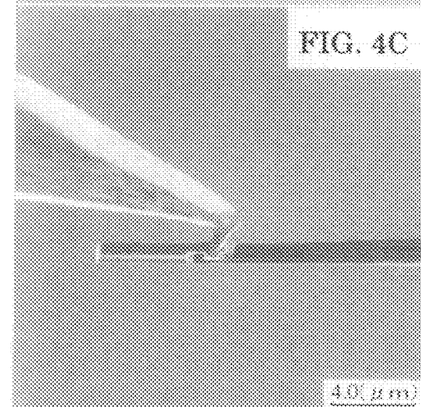
Figure 4D:
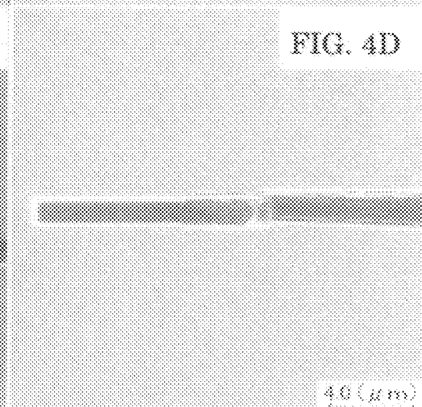
Figure 4E:
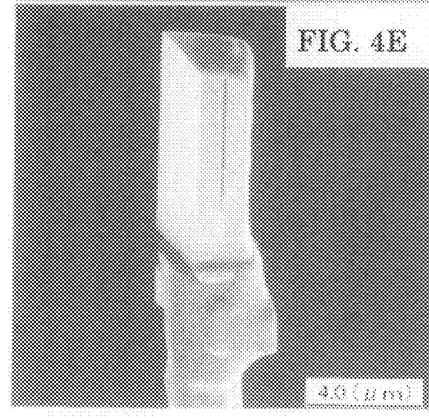
Figure 4F:
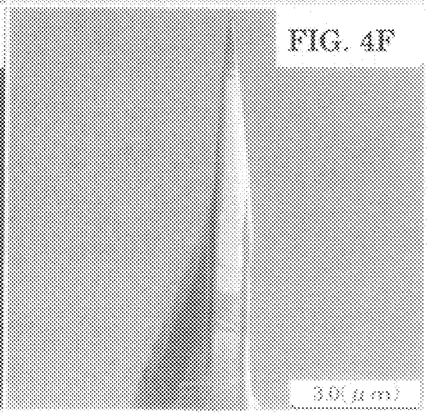

A next fifth step is a work meshing the sample piece 1 and the base needle 2, to which the concave/convex working is performed. An image shown in FIG. 4C is a place in which the observation sample piece 1 is transferred onto the base needle 2 by the fine probe 3 operated by the manipulator, and the concave/convex shape 4 is meshed. There can be observed the fact that the base part of this observation sample piece 1 is fixed to the tip part of the probe 3 by the deposition working. A sixth step is a work bonding both members by the deposition working after removing a deposition fixation portion of the probe 3 tip part by the FIB etching. An image of FIG. 4D is a state in which both members are connection-bonded by forming the deposition layer in a mesh region of both members. A seventh step is a work putting a mark specifying an observation site to a tip part of the sample piece 1 bonded on the base needle 2. An image of FIG. 4E is one in which the mark is put to the sample observation site in the tip part of the observation sample piece 1. In the image, since a left half of the cut-out block-like observation sample piece 1 is a silicon substrate and a specified site desired to be observed is a right side metal film formed on the substrate, a position of this mark is not a center of the block but is biased to the right side. In an eighth step, the FIB etching working of the observation sample piece 1 is applied such that the position of this mark becomes the needle point. In FIG. 4F, there is shown the sample whose sharpening working in the tip part was finished. The above are AP sample manufacturing procedures in which the technique of the invention is adopted. If the electric field is applied between this sample and the opposed leader electrode of the AP, the field evaporation occurs from the tip part of this sample, and it orderly proceeds in every atom layer from the surface first layer, so that by the AP it is possible to investigate the composition or the composition distribution of the interface, and additionally the electronic state change in every layer.

Figure 5:
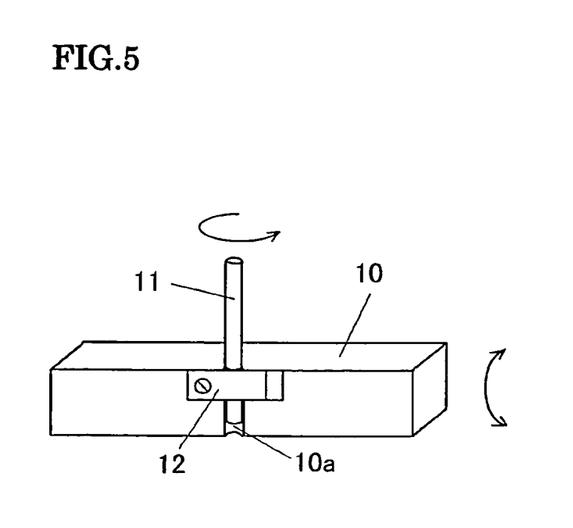
FIG. 5 is a view showing an example of a sample retention means used when the invention is implemented by an FIB apparatus.

Next, there is explained about an FIB apparatus of the invention, which implements the method of manufacturing the sample for the atom probe analysis. In order to apply the FIB working to the sample that is a needle-like body, there is demanded the fact that the member retaining the base needle possesses a function capable of rotating about the needle axis, and a function capable of switching a slant at least between 0° and 90°. In order to implement the method of manufacturing the sample for the atom probe analysis of the invention by a general-purpose FIB apparatus having a stage of a five-axis or six-axis drive, it is convenient to use such a sample holder as shown in FIG. 5 on a sample stage. In an embodiment shown in FIG. 5, there is prepared a jig in which a groove 10a, to which a metal tube 11 of copper or the like of about 1 mm φ is fitted, is formed in a position of a side face longitudinal direction center of a rectangular column 10 of about several cm in length and about 1 cm in thickness, and there is provided a leaf spring 12 nipping the fitted metal tube 11. This jig is fixed onto the sample stage of a conventional FIB apparatus by the deposition or the like. After the base needle 2 of the invention is inserted into this metal tube 11, it is fixed by caulking the metal tube 11. As to the base needle 2 retained by this jig, the five-axis or six-axis drive becomes possible. By this, there becomes one possessing the function capable of rotating about the needle axis, and the function capable of switching the slant at least between 0° and 90°, which are demanded as the FIB apparatus of the invention of the invention.

What is claimed is:

1. A method of making a sample for an atom probe analysis, the method comprising:

FIB etching to form a concave part in side walls of both a tip portion of a base needle and an end portion of a transplantation sample piece that extend perpendicular to a longitudinal axis of the base needle and the transplantation sample piece;

bonding the base needle and the transplantation sample piece by meshing the concave part to form a mesh joint, such that a continuous outer surface is formed in a direction of the longitudinal axis; and providing an FIB deposited film on the continuous surface to coat the meshed joint of the base needle and the transplantation sample piece.

2. A method of manufacturing a sample for an atom probe analysis according to claim 1, comprising a step in which the concave parts are manufactured so as to mutually mesh, and the FIB deposition film is provided under a state, such that the concave parts are mutually meshed around the meshed joint.

3. A method of manufacturing a sample for an atom probe analysis according to claim 1, wherein the concave part comprises a penetration groove between side walls of the base needle or the transplantation sample piece, or a convex part extending between the side walls.

4. A method of manufacturing a sample for an atom probe analysis, the method comprising:
- FIB etching to form an indentation in side walls of both a tip portion of a base needle and an end portion of a transplantation sample piece that extend perpendicular to a longitudinal axis of the base needle and the transplantation sample piece;
- bonding end faces of the base needle and the transplantation sample to form a butt joint; and
- forming an FIB deposited film overlying the butt joint and filling the indentations in the base needle and the transplantation sample piece,
- wherein the indentations are spaced away from the jointed faces of both of the base needle and the transplantation sample piece.

5. A method of making a sample for an atom probe analysis according to claim 4, wherein the concave part comprises a circumferential groove.

6. A method of making a sample for an atom probe analysis according to claim 4, wherein the indentations comprise a quadrate hole.

7. A method of manufacturing a sample for an atom probe analysis, the method comprising:
- FIB etching to form an indentation in side walls of both a tip portion of a base needle and an end portion of a transplantation sample piece that extend perpendicular to a longitudinal axis of the base needle and the transplantation sample piece,
- wherein the indentations further comprise a channel extending from end faces of the base needle and the transplantation sample piece parallel to the longitudinal axis of the base needle and the transplantation sample piece, each end of the channel terminating in a quadrate hole;
- bonding the end faces of the base needle and the transplantation sample to form a butt joint, such that channels in the base needle and the transplantation sample piece align with one another and the quadrate holes are spaced away from the butt joint; and
- forming an FIB deposited film overlying the butt joint and filling the indentations in the base needle and the transplantation sample piece.

* * * * *

UNITED STATES PATENT AND TRADEMARK OFFICE
CERTIFICATE OF CORRECTION

| | | |
|---|---|---|
| PATENT NO. | : 8,728,286 B2 | Page 1 of 1 |
| APPLICATION NO. | : 11/936417 | |
| DATED | : May 20, 2014 | |
| INVENTOR(S) | : Kaito | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1836 days.

Signed and Sealed this
Twenty-second Day of March, 2016

Michelle K. Lee
*Director of the United States Patent and Trademark Office*